United States Patent
Sridharan et al.

(10) Patent No.: US 6,949,112 B1
(45) Date of Patent: Sep. 27, 2005

(54) MEDICAL DEVICE FORMED OF POLYESTER COPOLYMER

(75) Inventors: Srinivasan Sridharan, Morgan Hill, CA (US); Timoteo Tomas, Union City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 640 days.

(21) Appl. No.: 09/917,024

(22) Filed: Jul. 26, 2001

(51) Int. Cl.$^7$ ............................................. A61M 29/00
(52) U.S. Cl. ..................................................... 606/194
(58) Field of Search ............................. 623/1.11, 1.18, 623/1.19, 1.44–1.51; 606/191–198

(56) References Cited

U.S. PATENT DOCUMENTS

| | | | |
|---|---|---|---|
| 4,584,353 A | 4/1986 | Kobayashi et al. | 525/438 |
| 4,670,498 A | 6/1987 | Furusawa et al. | 524/381 |
| 4,670,510 A | 6/1987 | Kobayashi et al. | 525/89 |
| RE32,983 E | 7/1989 | Levy | 428/36.92 |
| 5,264,260 A | 11/1993 | Saab | 428/35.5 |
| 5,306,246 A | 4/1994 | Sahatjian et al. | 604/96 |
| 5,439,443 A | 8/1995 | Miyata et al. | 604/96 |
| 5,797,877 A | 8/1998 | Hamilton et al. | 604/96 |
| 5,830,182 A | 11/1998 | Wang et al. | |
| 5,830,811 A | 11/1998 | Tang et al. | 442/216 |
| 5,849,846 A | 12/1998 | Chen et al. | 525/166 |
| 5,869,582 A | 2/1999 | Tang et al. | 525/415 |
| 5,871,468 A | 2/1999 | Kramer et al. | 604/96 |
| 6,071,835 A | 6/2000 | Tang et al. | 442/216 |
| 6,336,936 B2 | 1/2002 | Simhambhatla et al. | |
| 6,358,227 B1 | 3/2002 | Ferrera et al. | |
| 6,544,221 B1 * | 4/2003 | Kokish et al. | 623/1.11 |
| 6,632,883 B2 * | 10/2003 | Mayes et al. | 525/98 |

FOREIGN PATENT DOCUMENTS

EP        0 540 858        9/1992

* cited by examiner

*Primary Examiner*—Kevin T. Truong
(74) *Attorney, Agent, or Firm*—Fulwider Patton Lee & Utecht, LLP

(57) ABSTRACT

A medical device or component thereof, and particularly intracorporeal devices for therapeutic or diagnostic uses, formed at least in part of a copolymer having a hard block and a polylactone soft block. In a presently preferred embodiment, the hard block of the copolymer is a polyester, and more specifically, the copolymer comprises a di-block copolymer of poly(ethylene terephthalate) and polycaprolactone. The copolymer is suitable for forming a variety of medical devices or medical device components, and is preferably used to form a catheter balloon, such as a balloon for an angioplasty or stent delivery catheter. However, a variety of medical devices or medical device components can be formed of the copolymer, including stent covers, vascular grafts, and shaft components.

14 Claims, 2 Drawing Sheets

MEDICAL DEVICE FORMED OF POLYESTER COPOLYMER

BACKGROUND OF THE INVENTION

This invention generally relates to medical devices, and particularly to intracorporeal devices for therapeutic or diagnostic uses such as balloon catheters, stent covers, and vascular grafts.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In the design of expandable medical device components such as catheter balloons, the compliance of the component is an important consideration. Compliance is a measure of the extent of expansion in response to an increase in inflation pressure. Catheter balloons are typically classified as non-compliant, semi-compliant, and compliant, depending on the amount of radial expansion over a given inflation pressure range. Poly(ethylene terephthalate) (PET) is a conventional balloon material generally considered to have noncompliant or low compliant expansion, whereas materials such as polyethylene are typically considered to have compliant expansion. For many applications, intravascular catheter balloons should be formed from relatively strong materials in order to withstand the pressures necessary for various procedures without failing. Typically, this requires the use of a material that does not stretch appreciably, and which consequently necessitates that the deflated balloon material be folded around the catheter shaft in the form of wings, prior to inflation. However, it can be desirable to employ balloons, referred to as formed-in-place balloons, that are not folded prior to inflation, but which are instead expanded to the working diameter from a generally cylindrical or tubular shape (i.e., essentially no wings) having a nominal diameter that conforms to the catheter shaft.

In angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Stent covers on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as DACRON, may be implanted in vessels to strengthen or repair the vessel, or used in an anastomosis procedure to connect vessels segments together.

It would be a significant advance to provide a catheter balloon or other expandable medical device component with improved flexibility, strength and compliance characteristics.

SUMMARY OF THE INVENTION

This invention is directed to a medical device or component thereof, and particularly intracorporeal devices for therapeutic or diagnostic uses, formed at least in part of a copolymer having a hard block and a polylactone soft block. In a presently preferred embodiment, the hard block of the copolymer is a polyester and the soft block is a polylactone. More specifically, in one embodiment, the copolymer comprises a di-block copolymer of poly(ethylene terephthalate) and polycaprolactone. The copolymer is suitable for forming a variety of medical devices or components thereof, and is preferably used to form a catheter balloon, such as a balloon for an angioplasty or stent delivery catheter. However, a variety of medical devices or medical device components (hereafter, "the medical device") can be formed of the copolymer, including stent covers, vascular grafts, and shaft components.

In a presently preferred embodiment, the medical device is formed at least in part of a copolymer comprising a polyester hard block and a polylactone soft block (i.e., a block copolymer having one or more hard blocks or segments comprising a polyester and one or more soft blocks or segments comprising a polylactone). In one embodiment, the copolymer comprises a di-block copolymer. In alternative embodiments, the copolymer is a multi-block or random block copolymer. The terminology di-block is well understood in the art to refer to a copolymer having alternating, possibly randomized blocks. In contrast to a random block copolymer, the di-block copolymer has a long series of repeating units of the hard block followed by a long series of repeating units of the soft block. It can be represented as $(A)_n\text{-}(B)_m$ where there are n repeating units of hard block A and m repeating units of soft block B.

In one embodiment, the copolymer hard block is an aromatic polyester selected from the group consisting of poly(ethylene terephthalate), poly(ethylene naphthalate), poly(alkylene naphthalates), and poly(cycloalkylene naphthalates). However, in alternative embodiments, the copolymer hard block need not be a polyester. In one alternative embodiment, the hard block is a polyamide such as nylon 6, nylon 6,6, nylon 11, nylon 12, and nylon 6/10, a polyolefin such as polyethylene, polypropylene, polybutylene, or polyimides including aliphatic, aromatic, and heterocyclic polyimides. The hard block preferably comprises a crystalline polymer.

In one presently preferred embodiment, the copolymer lactone soft block is polycaprolactone. However, a variety of suitable lactones may be used including aliphatic lactones, valerolactones, and aromatic lactones.

Suitable polyester copolymers having a polyester hard block and a polylactone soft block for forming the medical device of the invention are available from AlliedSignal, and are described in U.S. Pat. No. 5,869,582, incorporated by reference herein in its entirety. The copolymers are made by reactive extrusion of the reactants such as, for example, poly(ethylene terephthalate) and lactone monomer, in a twin screw extruder, as disclosed in the U.S. Pat. No. 5,869,582 patent. The reactive extrusion process allows for formation of a copolymer, which in one embodiment is a di-block copolymer. In one embodiment, as set forth in the U.S. Pat. No. 5,869,582 patent, the di-block copolymer comprises (a) a first block of polyester wherein said first block is made from an aromatic polyester having: (i) an intrinsic viscosity which is measured in a 60/40 by weight mixture of phenol and tetrachloroethane and is at least about 0.8 deciliter/gram and (ii) a Newtonian melt viscosity which is measured by capillary rheometer and is at least about 7,000 poise at 280° C.; and (b) a second block of polyester wherein said second block is made from lactone monomer, wherein said aromatic polyester is in an amount of about 50 to about 99 weight percent and said lactone monomer is in an amount of about 1 to about 50 weight percent based on the diblock copolymer weight and said diblock copolymer has a melting point of at least about 230° C. Alternatively, the intrinsic viscosity of the aromatic polyester used to make the polyester first block is about 0.1 deciliter/gram to about 1.6 deciliter/gram.

The medical device or medical device component, which in accordance with the invention is formed of a copolymer having a hard block, and preferably a polyester hard block, and a polylactone soft block, has improved performance characteristics such as flexibility, trackability, strength, and compliance. The balloon of the invention has higher flexibility and trackability compared to catheter balloons formed of a relatively stiff material such as poly(ethylene terephthalate) (PET). Unlike catheter balloons formed PET blended with a compliance enhancing material, the medical device of the invention is formed of a copolymer. Thus, the lactone soft segment of the copolymer increases the flexibility and compliance of the balloon, without disadvantageously affecting properties such as the strength of the balloon which are provided by the hard segment. The compliance of the balloon or other device of the invention ranges from noncompliant (or low compliant) to compliant behavior, depending on various factors including the conditions used to form the balloon and the amount of the soft segment present in the copolymer. The amount of the soft segment can vary from 1 to about 99 weight % (wt %) of the weight of the copolymer, to produce a balloon having noncompliant, semi-compliant, or compliant radial expansion. The terminology low or noncompliant should be understood to refer to a balloon having a compliance of not greater than about 0.025 mm/atm over the working pressure range of the balloon, whereas semi-compliant refers to a balloon having a compliance of about 0.025 mm/atm to about 0.045 mm/atm over the working pressure range of the balloon, and compliant refers to a balloon having a compliance of greater than about 0.045 mm/atm over the working pressure range of the balloon.

One embodiment of the invention comprises a method of making a low profile, formed-in-place catheter balloon. The copolymer is extruded using a reactive extrusion process as disclosed in the U.S. Pat. No. 5,869,582, previously incorporated by reference herein, to thereby form tubing having a first outer diameter. The tubing is then blow molded by expanding the tubing in a balloon mold to a radially enlarged outer diameter. The expanded tubing is heat treated to relax the copolymer. Thus, the orientation of the copolymer molecules present following expansion in the balloon mold is lost during the heat treatment. Additionally, the expanded tubing heat shrinks during the heat treatment, so that the outer diameter reduces to, or nearly to, the original outer diameter of the tubing. As a result, a low profile balloon is formed with a nonexpanded configuration in which the deflated balloon is not folded around the catheter shaft for introduction and advancement within the patient's vasculature, i.e., it does not have significant wing formation. The balloon is therefore suitable for use as a formed-in-place balloon in which, after the balloon is heat shrunk according to the method of the invention, the balloon can be expanded to the working diameter within the patient's body lumen from a nonexpanded configuration to an expanded configuration. The balloon exhibits substantial elastic expansion within a first pressure range, and relatively little expansion within a second pressure range which is within a working pressure range of the balloon and which is greater than the first pressure range. Thus, the risk of over inflating the balloon within the body lumen is low. Moreover, the balloon, which in accordance with the invention is formed of the copolymer having a hard block and a lactone soft block, has low axial lengthening during the heat shrink step. As a result, the formed-in-place balloon has improved manufacturability and dimensional stability.

The medical device of the invention has improved flexibility, trackability, strength and compliance characteristics due to the copolymer having a hard block and a polylactone soft block. These and other advantages of the invention will become more apparent from the following detailed description when taken in conjunction with the accompanying exemplary drawings.

DETAILED DESCRIPTION OF THE INVENTION

Figure 1:
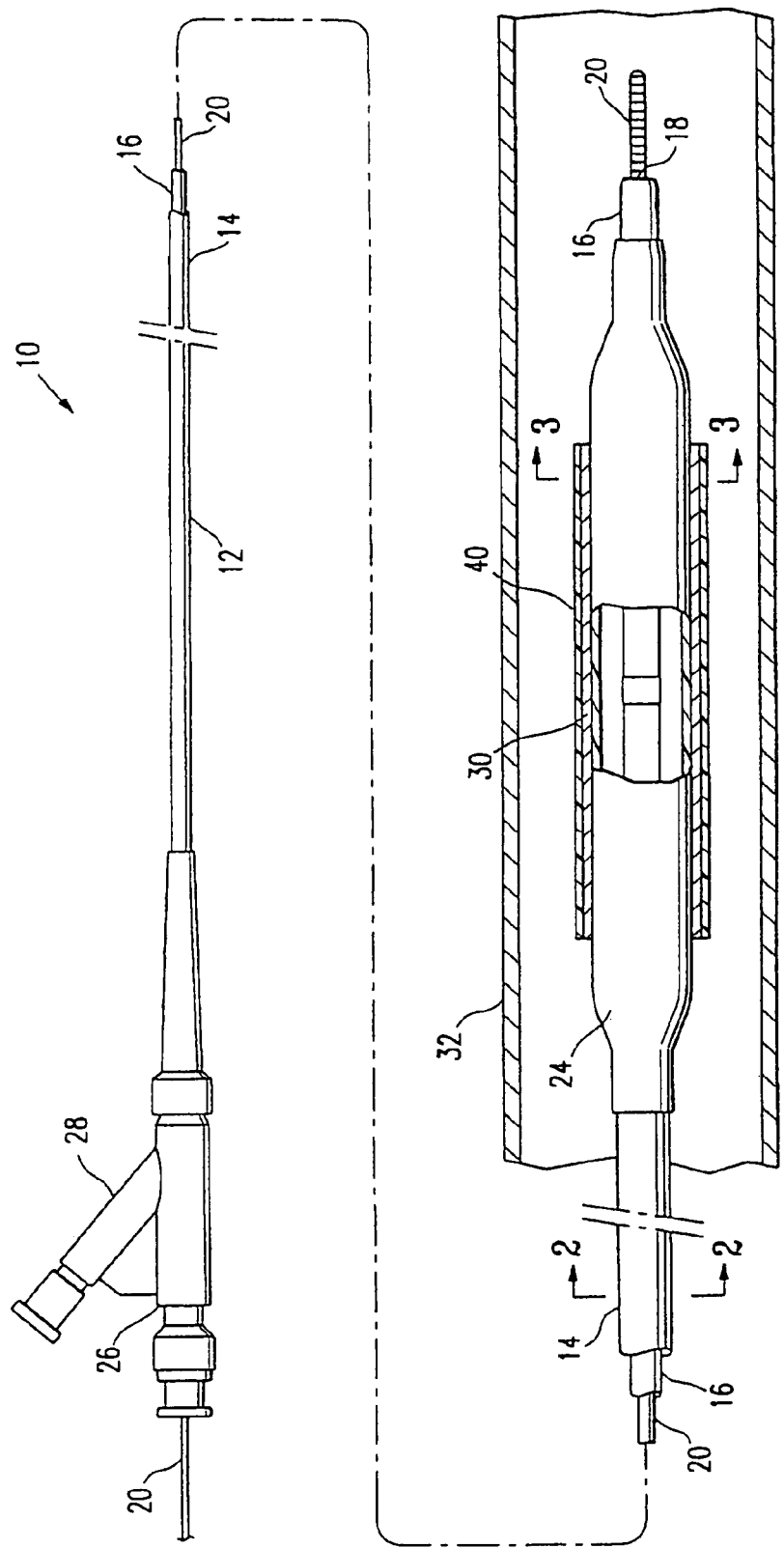
FIG. 1 is an elevational view, partially in section, of a stent delivery balloon catheter having a covered stent on the catheter balloon, which embodies features of the invention.
Figure 3:
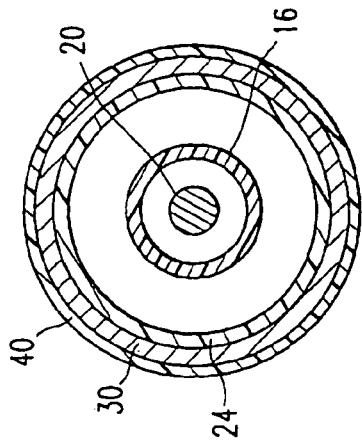
FIG. 3 is a transverse cross-section of the catheter shown in FIG. 1 taken at line 3—3, showing the covered stent disposed over the inflatable balloon.
Figure 2:
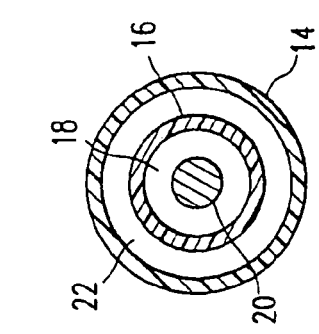
FIG. 2 is a transverse cross-section of the catheter shown in FIG. 1 taken at line 2—2.

FIGS. 1–3 illustrate an over-the-wire type stent delivery balloon catheter 10 embodying features of the invention. Catheter 10 generally comprises an elongated catheter shaft 12 having an outer tubular member 14 and an inner tubular member 16. Inner tubular member 14 defines a guidewire lumen 18 adapted to slidingly receive a guidewire 20. The coaxial relationship between outer tubular member 14 and inner tubular member 16 defines annular inflation lumen 22 (see FIGS. 2 and 3, illustrating transverse cross sections of the catheter 10 of FIG. 1, taken along lines 2—2 and 3—3 respectively). An inflatable balloon 24 is disposed on a distal section of catheter shaft 12, having a proximal shaft section sealingly secured to the distal end of outer tubular member 14 and a distal shaft section sealingly secured to the distal end of inner tubular member 16, so that its interior is in fluid communication with inflation lumen 22. An adapter 26 at the proximal end of catheter shaft 12 is configured to direct inflation fluid through arm 28 into inflation lumen 22 and to provide access to guidewire lumen 18. Balloon 24 has an inflatable working length located between tapered sections of the balloon, with an expandable stent 30 mounted on the balloon working length. FIG. 1 illustrates the balloon 24 in an uninflated configuration prior to deployment of the stent 30. The distal end of catheter may be advanced to a desired region of a patient's body lumen 32 in a conventional manner, and balloon 24 inflated to expand stent 30, seating the stent in the body lumen 32. A stent cover 40 is on an outer surface of the stent 30. Stent cover 40 generally comprises a tubular body, which preferably conforms to a surface of the stent and expands with the stent during implantation thereof in the patient. Although stent cover 40 is illustrated on an outer surface of the stent 30 in FIG. 1, the stent cover may be provided on all or part of an inner and/or an outer surface of the stent 30.

Balloon 24 is formed at least in part of a copolymer comprising a hard block and a polylactone soft block. In a presently preferred embodiment, the hard block is a polyester, and more specifically an aromatic polyester such as poly(ethylene terephthalate) (PET). In a presently preferred embodiment, the lactone soft block is polycaprolactone. Although discussed below primarily in terms of a PET/caprolactone copolymer, it should be understood that the copolymer may comprise a variety of suitable hard blocks including polyamides, polyolefins, polyimides, aromatic polyesters other than PET, and aliphatic polyesters, and a variety of suitable soft blocks including polyvalerolactone. Additionally, while discussed in terms of the presently preferred embodiment comprising a di-block copolymer, it should be understood that in alternative embodiments the copolymer is not a di-block copolymer.

In the embodiment illustrated in FIG. 1, the balloon 24 comprises a single layer formed of the PET/polycaprolactone copolymer. However, in alternative embodiments, the balloon 24 may have alternative polymers as additional layers on the PET/polycaprolactone copolymer layer, or blended with the PET/polycaprolactone copolymer.

The relative weight percentages of each component of the copolymer will vary depending on the desired characteristics of the balloon 24. In one embodiment, the amount of the polycaprolactone is about 10 wt % to about 20 wt %, preferably about 15 wt %, of the copolymer weight, and the amount of the PET is about 90 wt % to about 80 wt %, preferably about 85 wt %, of the copolymer weight. The balloon 24 formed therefrom has a low compliance of about 0.012 mm/atm to about 0.020 mm/atm over a working inflation pressure range of the balloon of about 8 atm to about 24 atm. The hoop strength of the balloon calculated for this example is about 30,000 psi to about 40,000 psi, preferably about 33,000 psi to about 36,000 psi. In another embodiment, the balloon 24 formed therefrom has a high compliance of about 0.030 mm/atm to about 0.045 mm/atm over a working inflation pressure range of the balloon from about 6 atm to about 14 atm. The hoop strength of the balloon 24 in this example is about 20,000 psi to about 30,000 psi, preferably about 25,000 psi to about 30,000 psi. The strength of the balloon 24, as reflected by the rated burst pressure of the balloon which is the inflation pressure at which the balloon will rupture, is about 8 atm to about 24 atm, preferably about 14 atm to about 18 atm. While discussed in terms of the balloon 24, the expansion of other expandable medical device components formed of the copolymer in accordance with the invention would be similar to the expansion of balloon 24.

The rated burst pressure of the balloon 24 depends on factors such as the blow up ratio (BUR) of the balloon, which is the balloon working outer diameter divided by the inner diameter of the tubing used to form the balloon. In a presently preferred embodiment, the BUR is about 7 to about 8, to produce a balloon having a rated burst pressure of about 20 atm to about 24 atm. A BUR of about 5 to about 6.5 produces a balloon with a lower rated burst pressure.

Balloon 24 is preferably formed from extruded tubing which is blow molded to form the balloon. Balloon 24 can be formed by conventional methods in which the blow molded balloon is attached to a catheter shaft, and the deflated balloon folded around the shaft for introduction and advancement within the patient's vasculature. Alternatively, the blow molded balloon may be further processed by heat shrinking the blow molded balloon prior to use, as is discussed in detail below. The extruded PET/polycaprolactone copolymer tubing used to form the balloon is extruded in a reactive extrusion process as disclosed in the U.S. Pat. No. 5,869,582, previously incorporated by reference herein. Specifically, the caprolactone monomer is injected into molten PET, and mixed in a twin screw extruder, with mixing and reaction times resulting in good mixing and a specific reaction time such that a copolymer is produced. Typically, a compatibilizer is not required, and the resulting copolymer has no separate phases of the PET or caprolactone, unlike a blend of the two materials.

One embodiment comprises a method of forming a formed-in-place catheter balloon, in which the blow molded balloon is heat shrunk before introduction of the catheter into the patient. The copolymer is extruded using the reactive extrusion process to form tubing having a first outer diameter, and the tubing is blow molded in a first balloon mold to form expanded tubing having a second outer diameter greater than the first outer diameter. The expanded tubing is then heat treated, to relax the orientation of the polymer molecules and reduce the outer diameter of the expanded tubing. Preferably, the expanded tubing is heat treated within a second balloon mold having a larger inner diameter than the first balloon mold, for example a 4.0 mm working inner diameter as opposed to a 3.0 mm working inner diameter mold used to form the expanded tubing, to prevent a direct contact of the expanded tubing with the heat or the metal of the balloon mold. The larger second balloon mold is used to produce uniform heating of the expanded tubing during heat treatment. The expanded tubing is preferably heated at about 160° C. to about 280° C., for about 5 seconds to about 120 seconds in the second balloon mold. As a result, the expanded tubing shrinks to, or nearly to, the original first outer diameter of the extruded tubing. Specifically, the expanded tubing outer diameter is reduced to about 120% to about 80% of the tubing first outer diameter. The expanded tubing is preferably axially stretched during the +heat treatment, however, in alternative embodiments no axial tension is applied during the heat treatment. The expanded tubing is preferably at atmospheric pressure and thus not expanded during the heat treatment, to allow the expanded tubing to heat shrink.

Unlike typical balloon materials in which the length of the expanded tubing will lengthen as the outer diameter of the expanded tubing is reduced during the heat shrinking thereof, the axial length of the polyester copolymer expanded tubing has little axial lengthening during the heat treatment. Specifically, the expanded tubing has an axial lengthening during the reduction of the outer diameter thereof of no more than about 10% to about 25% of the original length of the expanded tubing. In one embodiment, tubing having an outer diameter of about 0.032 inch (0.81 mm) and an inner diameter of about 0.014 inch (0.36 mm), is expanded in a first balloon mold to an outer diameter of about 0.114 inch (2.9 mm) and an inner diameter of about 0.113 inch (2.87 mm) and a length of about 18 mm. The expanded tubing is heat treated at about 230° C. to about 250° C. for about 30 seconds to about 60 seconds, to heat shrink the expanded tubing to an outer diameter of about 0.032 inch (0.81 mm) to about 0.034 inch (0.86 mm) and a length of about 20 mm to about 22, to thereby form the balloon.

The low profile balloon thus formed is attached to the catheter shaft 12 to form the balloon catheter 10. In FIG. 1, the balloon 24 is shown in a heat shrunk, low profile configuration prior to being inflated in the patient's body lumen 32. Although the balloon 24 illustrated in FIG. 1 has an observable working length with tapered sections between the working length and the proximal and distal skirt sections of the balloon, it should be understood that in other embodiments (not illustrated), the balloon of the invention in the heat shrunk, low profile configuration has a heat shrunk, uniform outer surface without the tapered sections illustrated in FIG. 1. As a result of the heat treatment, the balloon does not have deflated wings folded around the balloon for introduction and advancement within the patient's vasculature. The balloon 24 is inflated in the body lumen 32 from the heat shrunk outer diameter, unlike a balloon which is introduced into the body lumen in the blow molded configuration. The stress strain curve of the balloon allows the balloon to be inflated within the body lumen from the heat shrunk diameter to a working diameter having the same dimensions originally present in the blow molded expanded tubing prior to the heat treatment. The balloon exhibits substantial elastic expansion within a first pressure range, and relatively little expansion within a second pressure range which is within a working pressure range of the balloon and which is greater than the first pressure range. In a method of performing a medical procedure, such as dilatation of a stenosis or expanding a stent, the balloon 24 is typically first inflated within the first pressure range. Thereafter, the balloon 24 can be inflated within the second pressure range without over expanding the balloon and damaging the blood vessel, due to the lower compliance of the balloon in the second pressure range (Question: is this correct?). The first pressure range is preferably about 1 atm to about 16 atm, and the second pressure range is preferably about 16 atm to about 24 atm.

Figure 5:
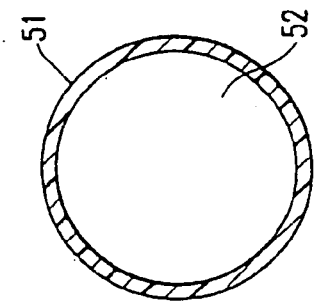
FIG. 5 is a transverse cross-section of the graft or cover shown in FIG. 4, taken along lines 5—5.
Figure 4:
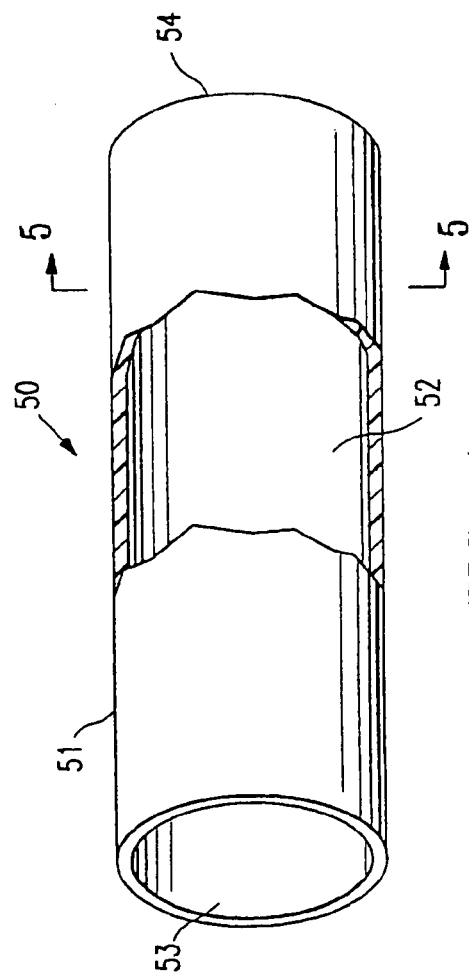
FIG. 4 is an elevational view, partially in section, of a vascular graft or stent cover which embodies features of the invention.

Although discussed primarily in terms of a catheter balloon, the medical device formed of the copolymer can be a variety of medical devices, and preferably expandable medical devices, such as a stent cover or a vascular graft. FIG. 5 illustrates a vascular graft 50, generally comprising a tubular body 51 having a lumen 52 therein, and ports 53, 54 at either end of the graft 50. The graft 50 is configured for being implanted in the patient, and it may be expanded into place within a vessel, or surgically attached to a vessel such as to a free end or a side wall of a vessel. The graft 50 length is generally about 4 to about 80 mm, and more specifically about 10 to about 50 mm, depending on the application, and wall thickness is typically about 2.5 μm to about 25 μm, preferably about 5 μm to about 15 μm. The diameter is generally about 1 to about 35 mm, preferably about 3 to about 12 mm, depending on the application. Stent cover 40 is similar to vascular graft 50, except it is on a stent as illustrated in FIG. 1.

While the present invention is described herein in terms of certain preferred embodiments, those skilled in the art will recognize that various modifications and improvements may be made to the invention without departing from the scope thereof. For example, in the embodiment illustrated in FIG. 1, the catheter is over-the-wire stent delivery catheter. However, one of skill in the art will readily recognize that other types of intravascular catheters may be used, including balloon angioplasty catheters and rapid exchange balloon catheters. Rapid exchange balloon catheters have a distal guidewire port and a proximal guidewire port and a short guidewire lumen extending between the proximal and distal guidewire ports in a distal section of the catheter. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A medical device or component thereof formed at least in part of a copolymer, the copolymer comprising:
    a) a polyester hard block selected from the group consisting of poly(ethylene terephthalate), poly(ethylene naphthalate), poly(alkylene naphthalates), and poly(cycloalkylene naphthalates); and
    b) a polylactone soft block.

2. The medical device of claim 1 wherein the polylactone block is polycaprolactone.

3. The medical device of claim 1 wherein the copolymer comprises a di-block copolymer of poly(ethylene terephthalate) and polycaprolactone.

4. The medical device of claim 1 wherein the medical device is selected from the group consisting of a stent cover, a vascular graft, and a catheter balloon.

5. A catheter balloon formed at least in part of a copolymer, the copolymer comprising:
    a) a polyester hard block selected from the group consisting of poly(ethylene terephthalate), poly(ethylene naphthalate), poly(alkylene naphthalates), and poly(cycloalkylene naphthalates); and
    b) a polylactone soft block.

6. The catheter balloon of claim 5 wherein the copolymer comprises a copolymer of poly(ethylene terephthalate) and polycaprolactone.

7. The catheter balloon of claim 5 wherein the copolymer comprises a di-block copolymer.

8. The catheter balloon of claim 5 wherein the amount of the polylactone is about 1 wt % to about 99 wt % of the copolymer weight.

9. The catheter balloon of claim 5 wherein the polylactone block is polycaprolactone.

10. The catheter balloon of claim 9 wherein the amount of the polycaprolactone is about 10 wt % to about 20 wt % of the copolymer weight.

11. The catheter balloon of claim 10 wherein the balloon has a low compliance of about 0.012 mm/atm to about 0.02 mm/atm at an inflation pressure of about 8 atm to about 24 atm.

12. The catheter balloon of claim 10 wherein the balloon has a low compliance of about 0.03 mm/atm to about 0.045 mm/atm at an inflation pressure of about 8 atm to about 18 atm.

13. The catheter balloon of claim 5 wherein the balloon is formed from balloon tubing extruded in a reactive extrusion process.

14. A balloon catheter, comprising:
 a) an elongated shaft having a proximal end, a distal end, a distal shaft section, and an inflation lumen; and
 b) an inflatable balloon on the distal shaft section with an interior in fluid communication with the inflation lumen, the balloon being formed at least in part of a copolymer having a hard block selected from the group consisting of polyamide, polyimide, and polyolefin, and a polylactone soft block.

\* \* \* \* \*

UNITED STATES PATENT AND TRADEMARK OFFICE
CERTIFICATE OF CORRECTION

PATENT NO.   : 6,949,112 B1
DATED        : September 27, 2005
INVENTOR(S)  : Srinivasan Sridharan et al.

It is certified that error appears in the above-identified patent and that said Letters Patent is hereby corrected as shown below:

Column 6,
Line 58, delete "+heat" and insert -- heat --.

Column 7,
Lines 51-52, delete "(Question: is this correct?)".

Signed and Sealed this

Twenty-fourth Day of January, 2006

JON W. DUDAS
*Director of the United States Patent and Trademark Office*